United States Patent [19]

Hibbeln

[11] Patent Number: 5,611,345

[45] Date of Patent: Mar. 18, 1997

[54] MEDICAL INSTRUMENT WITH IMPROVED ULTRASONIC VISIBILITY

[76] Inventor: John F. Hibbeln, 4433 Washington St., Downers Grove, Ill. 60513

[21] Appl. No.: 427,741

[22] Filed: Apr. 24, 1995

[51] Int. Cl.$^6$ .................................................. A61B 8/00
[52] U.S. Cl. .................................................. 128/662.05
[58] Field of Search ............... 128/660.03, 662.03, 128/662.05, 662.06; 604/272, 273

[56] References Cited

U.S. PATENT DOCUMENTS

| | | |
|---|---|---|
| 2,803,587 | 4/1958 | Everett . |
| 3,090,384 | 5/1963 | Baldwin et al. . |
| 3,955,558 | 5/1976 | Fuisz . |
| 4,401,124 | 8/1983 | Guess et al. . |
| 4,582,061 | 4/1986 | Fry . |
| 4,869,259 | 9/1989 | Elkins . |
| 4,977,897 | 12/1990 | Hurwitz . |
| 5,048,530 | 9/1991 | Hurwitz . |
| 5,081,997 | 1/1992 | Bosley, Jr. et al. . |
| 5,249,580 | 10/1993 | Griffith ........................... 128/662.06 |
| 5,421,336 | 6/1995 | De Bernardis .................. 128/662.05 |

OTHER PUBLICATIONS

Moulton et al., *Radiology*, vol. 186, No. 2, pp. 515–522, Feb. 1993.
Peter N.T. Wells, *Advances in Ultrasound Techniques and Instrumentation*, Churchill Livinstone, 1993.
Product brochure, C.R. Bard, Inc., "Core Tissue Biopsy Using the Bard® Biopsy® System," 1994.

*Primary Examiner*—George Manuel
*Attorney, Agent, or Firm*—Brinks Hofer Gilson & Lione

[57] ABSTRACT

A medical instrument, and in particular, a needle, having improved reflective properties and enhanced ultrasonic visibility when used in conjunction with an ultrasonic imaging system is disclosed. The medical instrument has a non-circular shaped portion adapted for insertion into the body, the non-circular shaped portion comprising at least one exterior planar surface capable of reflecting an incident ultrasonic beam.

10 Claims, 2 Drawing Sheets

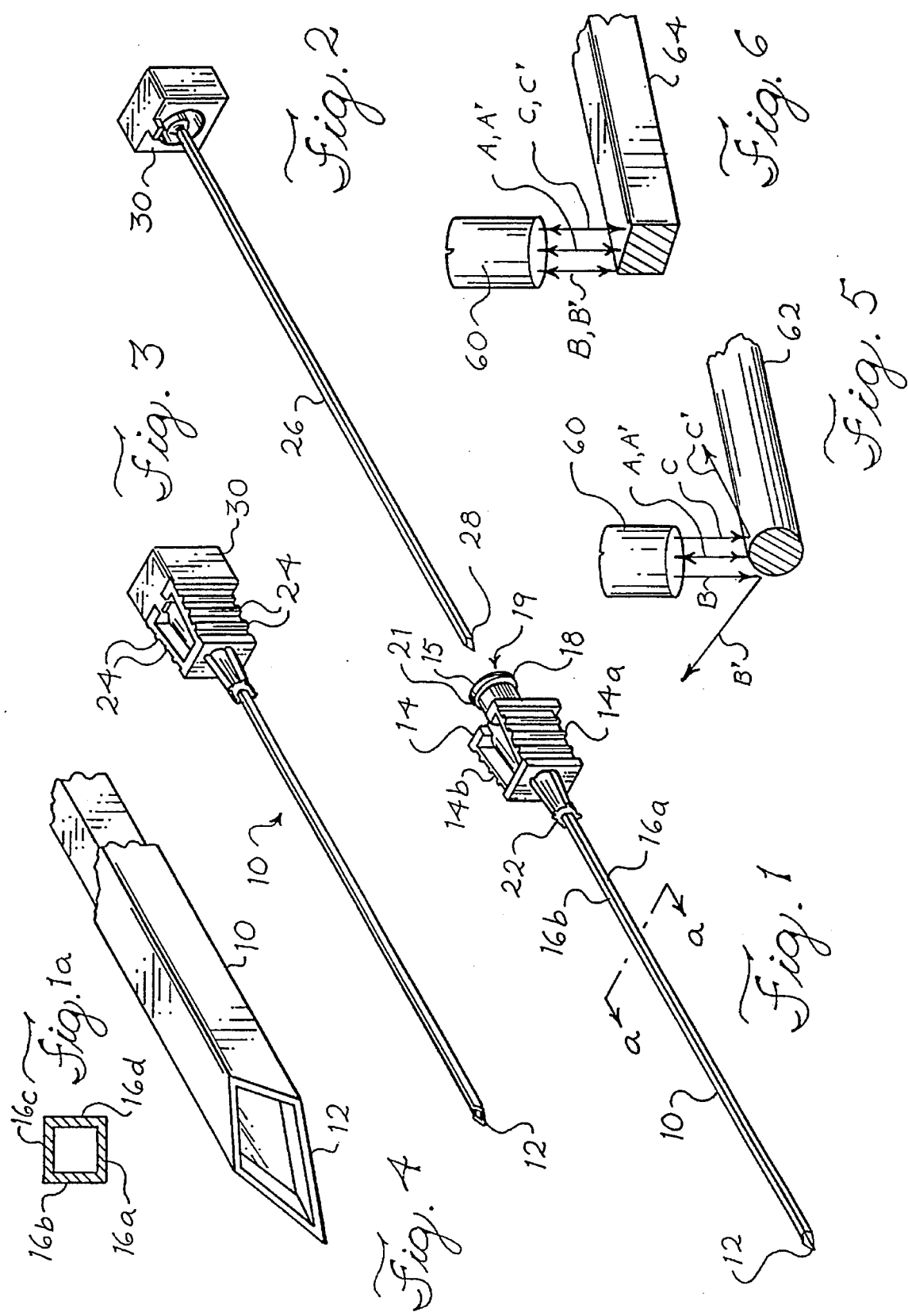

ULTRASOUND MONITOR DISPLAY

MEDICAL INSTRUMENT WITH IMPROVED ULTRASONIC VISIBILITY

This invention relates generally to the medical arts and more particularly to a needle or other medical instrument having improved reflective properties and enhanced ultrasonic visibility when used in conjunction with an ultrasonic imaging system.

BACKGROUND OF THE INVENTION

Many techniques have been developed to non-invasively image or "see" the internal structures of human and animal bodies. Such techniques have in the past included radiography, fluoroscopy, and, more recently, ultrasonography, computed tomography, and magnetic resonance imaging. Prior to the development of these imaging techniques, exploratory surgery had to be performed in order to see the internal structures of human and animal bodies. However, fatal complications were sometimes encountered with exploratory surgery.

Despite the advances that have been made in the above imaging techniques, many entities are difficult to differentiate using only imaging techniques. Accordingly, it is often very difficult to conclusively diagnose certain conditions based solely on their image. Only by obtaining a sample of the involved tissue or fluid can the condition or entity be conclusively identified, and the correct diagnosis made.

In attempt to avoid the dangers associated with surgery, a number of minimally invasive techniques for obtaining tissue or fluid samples from the body have been developed in recent years. These techniques involve the use of imaging techniques, such as ultrasound, to guide specially designed needles through the inside of the body to the target tissue or fluid. Once guided to the target, the specially designed needle is used to obtain samples of the target tissue or fluid for analysis outside of the body. Moreover, in certain circumstances, a tube or catheter may be installed at the target for longer term fluid drainage or for administering therapeutic agents. Many lives have been saved and surgical complications avoided by the use of such imaging guidance techniques for obtaining tissue or fluid samples from the body.

In tissue biopsy, for example, a needle (or puncturing cannula) is inserted into the body and guided to the site of the tumor or other tissue mass to be evaluated. The physician guides the needle to the desired location in the body using an imaging system such as ultrasound, which permits the physician to monitor the insertion and advancement of the needle in the body. Ultrasound guidance systems are well known in the art, and work on the principle of reflecting sound waves off of the needle. The reflected wave is detected by a monitor located outside the body, and an image is generated, which reveals the location of the needle in the body. Two examples of ultrasonically guided puncturing cannula apparatuses are found in U.S. Pat. No. 3,556,079 and U.S. Pat. No. 4,029,084, the disclosures of which are incorporated herein by reference. Needle guidance with ultrasound imaging may be used to obtain tissue and fluid samples in a variety of procedures such as, for example, para and thoracocenteses, amniocentesis, abscess aspiration, cytologic and core histologic biopsy, and fetal blood sampling.

Accurate guidance of the needle in the body is not only critical to obtaining the proper tissue sample, but accurate guidance is also necessary to avoid unintentional puncturing or damage to body tissue. Unfortunately, needles conventionally used in biopsy procedures and the like that rely on ultrasonic imaging for guidance have relatively poor ultrasonic visibility. The needles conventionally used in such procedures have a generally tubular shape with a circular cross-section, and thus present a curved surface to the incident ultrasonic beam. When the incident beam strikes the curved surface of these conventionally shaped circular needles, only a small portion of the beam is reflected back to the monitoring device; a majority of the incident beam being scattered away from the monitoring device. Because only a small portion of the reflected incident beam is detected at the monitoring device, a relatively poor image of the needle is generated, which makes it difficult to ascertain the precise position of the needle in the body. In response to this problem, considerable effort has been expended to enhance the ultrasonic visibility of conventionally shaped circular needles.

For example, one prior approach to enhancing the ultrasonic visibility of the needle is roughening or scouring the outer surface of the needle itself or by roughening the surface of a solid stylet that is disposed axially within the lumen of the needle. One such example of this approach is found in U.S. Pat. No. 4,869,259, the disclosure of which is incorporated herein by reference. A portion of the exterior surface of the needle is uniformly and randomly particle-blasted with particulate materials such as sand, silicon carbide, or metal silicates. The resulting particulate band, which extends around the circumference of the needle, increases its ultrasonic visibility by causing diffraction of the reflected incident beam as the angle between the needle and the incident beam is deviated from 90 degrees.

Another example of an attempt to make a needle more ultrasonically visible is found in U.S. Pat. No. 4,401,124, the disclosure of which is incorporated herein by reference. This patent discloses a surgical instrument having diffraction grating disposed on the surface of the instrument. The grating has a specific distance between the depths of adjacent grooves, the distance being a function of various parameters including the wavelength of the incident beam and the angle between the incident beam and an axis along the surface of the instrument. It is disclosed that the diffraction grating increases the reflection coefficient of the surgical instrument, which increases its ultrasonic visibility.

Although these prior art approaches may improve the ultrasonic visibility of a needle, the process of roughening or scouring the needle adds additional steps to the manufacturing process, and increases manufacturing costs. Also, a scoured or roughened needle surface may complicate percutaneous insertion and subsequent passage of the needle through body tissue.

Another approach to increasing the ultrasonic visibility of a needle is disclosed in U.S. Pat. No. 5,048,530, the disclosure of which is incorporated herein by reference. That patent discloses a needle or other tubular cannula having one or more "sounding apertures" positioned along the needle to improve its ultrasonic visibility. The diameter of each sounding aperture is substantially equal to a predetermined wavelength of an incident ultrasonic beam. According to the disclosure of the patent, upon striking the sounding aperture, the incident beam is diffracted and the resulting echo diffuses isotopically therefrom, thereby improving the ultrasonic detectability of the needle. Again, as with other prior art approaches, the sounding aperture approach may make the needle more difficult to manufacture and increase manufacturing costs.

Another approach to improving the ultrasonic visibility of a needle is to place a transducer in the needle itself to radiate an ultrasonic beam back to a detector located outside the body. However, a shortcoming to this approach is that the needle must be equipped with expensive and complicated electronic circuitry, which increase the complexity of and the cost to manufacture the needle.

Clearly, there is a need for a medical instrument, and a needle in particular, with enhanced ultrasonic visibility, and which is inexpensive and simple to manufacture.

SUMMARY OF THE INVENTION

Applicant has developed a medical instrument, which satisfies the need for such an instrument with enhanced ultrasonic visibility. As described in more detail below, a medical instrument such as a needle is provided comprising a non-circular shaped portion having at least one exterior planar surface. The planar surface of the needle provides a greater surface area than that presented by conventionally shaped circular needles for reflecting an incident beam. Because of the greater surface area, a greater amount of the incident beam is reflected back to a monitoring device, thereby enhancing the visibility of the needle. Thus, the needle of this invention is more readily "seen" by ultrasonic imaging techniques than conventionally shaped circular needles.

In accordance with one aspect of the invention, a medical instrument for insertion into the body and adapted to be used in conjunction with an imaging system is provided. The medical instrument comprises a noncircular shaped portion which is to be inserted into the body, the noncircular portion having at least one exterior planar surface capable of reflecting an incident beam of energy.

In another aspect of the invention, a method of monitoring the location of a percutaneous positioned medical instrument is provided. A medical instrument having a percutaneous positioned non-circular shaped portion comprising at least one exterior planar surface is provided. An incident beam of energy is directed at the exterior planar surface of the medical instrument such that the incident beam is reflected. The reflected incident beam is then received and monitored by a monitoring device.

Further aspects of the present invention will be apparent to those skilled in the art based on the following detailed description of a preferred embodiment of the invention and the accompanying drawings.

BRIEF DESCRIPTION OF THE DRAWINGS

FIG. 1 is a perspective view of a preferred needle of the invention.

Fig. 1a is a cross-section view of the needle illustrated in FIG. 1 along line a—a.

FIG. 2 is a perspective view of a solid stylet wire adapted for placement within the inner lumen of the needle illustrated in FIG. 1.

FIG. 3 is a perspective view of the needle illustrated in FIG. 1 with the solid stylet wire illustrated in FIG. 2 sitting within the inner lumen of the needle.

FIG. 4 is a cutaway elevational view of a preferred needle of the invention having a solid stylet axially disposed therein.

FIG. 5 is a schematic representation of an incident beam of energy being reflected from a conventionally shaped circular needle.

FIG. 6 is a schematic representation of an incident beam of energy being reflected from a preferred needle of the present invention having a square-shaped cross-section.

DETAILED DESCRIPTION OF THE PRESENTLY PREFERRED EMBODIMENTS

The accompanying drawings are provided solely for the purpose of illustrating a presently preferred embodiment of the invention and are not intended to limit the scope of the invention in any way.

Figure 7:
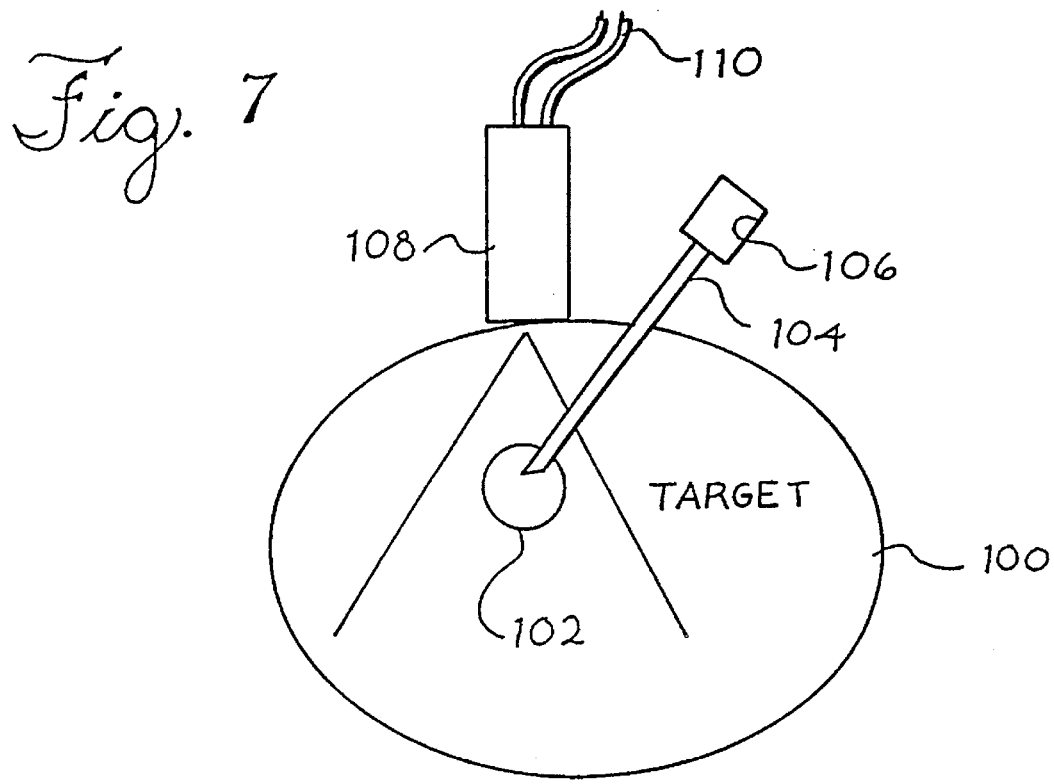
FIG. 7 is a schematic representation of the use of a preferred needle of the invention with an ultrasound system.
Figure 8:
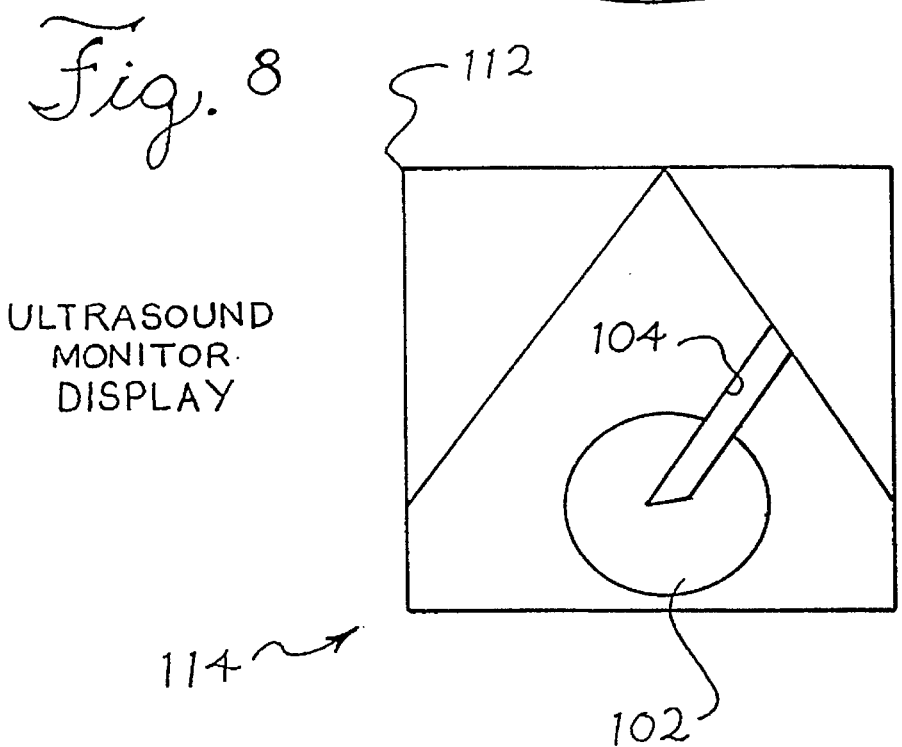
FIG. 8 is a schematic representation of how a preferred needle of the invention appears on the monitor of an ultrasound system.

FIGS. 1–4 show the external configuration of a preferred needle of the present invention while FIGS. 5 and 6 illustrate the means by which a preferred needle of the invention provides improved ultrasonic visibility. FIGS. 7 and 8 schematically depict a preferred needle of the invention in combination with an ultrasound system and the image generated by a preferred needle of the present invention, respectively.

With reference to FIGS. 1–4, a preferred needle of the present invention comprises a hollow needle body 10 having a beveled distal tip 12 and a proximal connecting hub 14 formed on opposite ends of the needle body 10. In a preferred aspect of the invention, the needle body 10 has a square-shaped cross-section with planar exterior surfaces 16a, 16b, 16c, and 16d (see FIG. 1a). The planar exterior surface is preferably continuous along a substantial portion of the length of the needle body as shown. It should be understood, however, that the needle of the present invention may be of any non-circular cross-section shape that has at least one exterior planar surface for reflecting an incident beam of energy. Thus, other suitably shaped needles contemplated for use in this invention may have a triangular cross-section, a pentagonal cross-section, a hemispherical cross-section, etc. Unlike the needle body 10, however, the shape of the needle tip 12 is not critical. Numerous types of needle tips are contemplated for use in this invention such as, for example, beveled tips, double beveled tips, and conical tips.

The needle body 10 is configured with a length and cross-section depending on the procedure and the desired depth of percutaneous insertion of the needle. For example, for histologic biopsies of the liver or kidney where a large biopsy is required, a relatively large needle having a size similar to an about 14 gauge conventionally shaped circular needle is preferred. On the other hand, fluid aspiration (such as in amniocentesis) or cytologic aspiration calls for a relatively small biopsy sample, and thus a smaller needle having a size similar to an about 20 gauge conventionally shaped needle is preferred. The needle body 10 is preferably made from any medical grade material such as those marketed as Superior "microbore" or Sterling "plug drawn."

The connecting hub 14 is preferably made from a clear plastic material. The connecting hub preferably comprises two opposing faces 14a and 14b (not shown). The connecting hub 14 further comprises a channel 15 (not shown) defined by a female connector arm 18. The female connector arm 18 has a first opening 19 which leads to the channel 15. A flange 21 extends around the opening 19 of connector arm 18. The female connector arm 18 has a second opening 22 adapted to receive the needle body 10. The channel 15 extends along a longitudinal axis of connecting hub 14 and communicates with the inner lumen of needle body 10. Finally, three annular ribs 24 extend laterally across the opposing faces 14a and 14b (not shown) of the connecting hub 14 to form convenient finger gripping surfaces whereby the needle may be firmly grasped by the operator during insertion and manipulation of the needle.

Although not critical in the present invention, a solid stylet wire 26, (shown separately in FIG. 2), may optionally be axially disposed within the inner lumen of the needle body 10. The solid stylet wire comprises a solid tip 28 which preferably corresponds in configuration to the distal tip 12 of the needle body 10. In the embodiment illustrated in the drawings, the solid stylet wire has a solid beveled tip 28, which corresponds with the beveled tip 12 of the needle body 10. The stylet wire 26 is axially disposed within the inner lumen of the needle body 10 so that the beveled distal tip 28 of the solid stylet wire 26 resides fully within and flush with the open bevel tip 12 of the surrounding needle body 10. The solid stylet wire 26 is most preferably shaped so that it can sit fully within and flush with the needle body 10. Thus, with respect to the embodiment illustrated in the drawings, the solid stylet 26 preferably has a square-shaped cross-section. As those skilled in the art will appreciate, the stylet may be modified to have a variable length trough or cut-out for use in obtaining core tissue samples.

A color coded obturator cap 30 is fixed to the distal end of the solid styler wire 26 and is configured to fully cover the opening 19 of the female connector arm 15 of the connecting hub 14 when the solid stylet wire 26 is fully distally advanced in the inner lumen of the needle body 10. By covering the opening 19, the obturator cap 30 will prevent contaminants from entering the channel 15 of connecting hub 14 and the inner lumen of the needle body 10.

The surgical instrument of the present invention is especially adapted for use in combination with an ultrasonic imaging system. A discussion of techniques for using ultrasonic imaging systems in needle guidance is provided in the book titled "Advances in Ultrasound Techniques and Instrumentation," edited by Peter N. T. Wells, published by Churchill-Livingstone, 1993 (see specifically Chapter 7, Needle Guidance Techniques, by W. Norman McDicken), the disclosure of which is incorporated herein by reference. Generally, ultrasonic imaging systems emit a low frequency incident beam of about 2 to 10 MHz from a transducer through the body tissue. The incident beam is reflected by the needle, and the reflected beam travels back through the body tissue and is detected by a monitor positioned outside the body (in the more modern ultrasonic imaging systems the transducer is also the detector). An image of the needle is generated by the imaging system using the reflected incident beam, thereby enabling the operator to ascertain the position of the needle in the body.

Generally, where small biopsies are performed at shallow depths (e.g., about 1–5 c.m.) the ultrasound imaging system uses about a 7–10 MHz transducer to generate the incident beam. For larger biopsies performed at deeper depths (e.g., about 5–15 c.m.), 5–2 ½ MHz transducers are preferred.

FIGS. 5 and 6 illustrate how a preferred needle of the present invention achieves better ultrasonic visibility than conventionally shaped circular needles. FIG. 5 shows an ultrasonic beam being geometrically reflected from the outer wall of a conventionally shaped circular needle 62. A transducer 60 is positioned in relation to the needle 62. The incident ultrasonic beam emanating from the transmitter 60 is indicated by arrows A, B, and C respectively. As depicted in FIG. 5, the incident beam strikes the surface of the conventionally shaped circular needle and is reflected as indicated by arrows A', B', and C', respectively. As can be ascertained from FIG. 5, only a small portion of the incident beam (e.g., represented by arrow A') is reflected back to transducer 60 for detection. The majority of the incident beam (e.g., represented by arrows B' and C', respectively) is reflected in a direction away from the transducer 60 and thus is not detected. Thus, the arrangement depicted in FIG. 5 would result in poor visualization of the conventionally shaped circular shaped needle by the imaging equipment (not shown) to which the transducer is attached.

Conversely, the arrangement in FIG. 6 provides for substantially improved visualization of a preferred needle of the present invention. The planar surface provided by a preferred needle of the invention presents a much larger surface area for the incident beam to strike in a manner such that the beam is reflected back to the transducer for detection. As can be ascertained from FIG. 6, a majority of the reflected incident beam (A', B', and C') is directed back to the transducer 60 when it strikes the planar surface 64 of a preferred needle of the invention. This, of course, leads to better visualization of the needle by the imaging equipment (not shown) to which the transducer is attached. Additionally, by spinning the preferred needle of the invention during insertion, it is possible to create a micro-cavitation effect, which improves the ultrasonic visibility of the needle.

Finally, FIGS. 7 and 8 are schematic representations of a needle according to the invention in combination with an ultrasonic imaging system. A needle 104 according to the invention is inserted into a human body 100 (illustrated in cross-section) and is guided to a target area 102 by an ultrasonic imaging system. The ultrasonic imaging system comprises a transducer 108, a transducer cable 110, and ultrasound monitor display 114. An image 112 of the needle 104 and the target area 102 is generated on the ultrasound monitor display 114, which enables the operator to guide the needle 104 to the target area 102.

As those skilled in the art will appreciate based on the foregoing description, a variety of needles such as fluid aspiration needles (such as amniocentesis needles) and biopsy needles may be adapted for use in this invention. Also, the needles of the present invention may be adapted for use in various biopsy techniques, including cytologic aspiration, fluid aspiration, histological biopsies, and coaxial percutaneous biopsy techniques. Additionally, the needles of the present invention may be used in automated biopsy devices such as, for example, the Bard® Biopty® System.

Furthermore, the present invention may be adapted for use with medical instruments other than just needles wherever improved ultrasonic visibility is desired. For example, trocars, insertable scopes, catheters, and the like may be provided with a non-circular cross sectional shape having at least one exterior planar surface for reflecting an incident beam. Finally, although the present invention is especially adapted for use with ultrasonic imaging systems, it may also be used with imaging systems such as x-ray imaging systems, CAT scan imaging systems, and the like.

EXAMPLE

Phantom ultrasounds were conducted using the following materials.

Test Materials: A container of metamusal and a canned ham;

Needles: Conventional circular-shaped needles ranging in size from 22 to 18 gauge, and preferred needles of the invention having a square-shaped cross-section with a size corresponding to the projected cross-sectional area of the circular shaped needles;

Transducers: 4 MHz variable frequency phased array vector ultrasound transducer and a 7 MHz variable frequency phased array linear ultrasound transducer with an Acuson Corporation (Mountain View, Calif.,) 128 X/P 10 ultrasound platform. The ultrasound images were recorded on an Acuson Corporation Aegis image archival system.

Also, the angle between the needle and incident beam was varied in the phantom ultrasounds. The angles tested were 90 degrees, 45 degrees, 30 degrees, and 15 degrees.

In the phantom ultrasounds, the images generated by the preferred needles of the present invention were consistently better than the conventional circular-shaped needles. As expected, the images generated by all the needles were best when the angle between the incident beam and the needle was 90 degrees. The image became increasingly poorer as the angie was varied from 45 degrees to 30 degrees, and was at its poorest at 15 degrees. The difference between the images generated by the preferred needles of the invention and conventional circular-shaped needles were most pronounced with larger needles (e.g., lower gauge), at higher frequencies, and the more superficially located (e.g., closer to the surface) the needle was in the test material.

The foregoing description, examples, and drawings, which describe a preferred embodiment of the present invention, are to be considered as illustrative and not restrictive in character. The invention, the full scope of which, is defined by the following claims.

I claim:

1. A method of monitoring the location of a percutaneous positioned needle comprising:

a) providing a percutaneously positioned needle, the needle comprising a body and a distal tip wherein the needle body comprises a non-circular cross-section and, a planar surface;

b) directing an incident beam of energy at the planar surface of the needle body such that the incident beam of energy is reflected; and c) receiving and monitoring the reflected beam.

2. The method of claim 1 wherein the incident beam comprises an ultrasonic beam.

3. The method of claim 2 wherein the needle comprises a biopsy needle.

4. The method of claim 2 wherein the needle comprises a fluid aspiration needle.

5. The method of claim 2 wherein the needle body comprises a square cross-section.

6. The method of claim 5 wherein the needle body comprises a hollow body and a stylet positioned within the hollow body.

7. The method of claim 1 wherein the planar surface is continuous along a substantial portion of the length of the needle body.

8. A combination of a needle for insertion into the body and an ultrasonic imaging system adapted to direct an incident beam of ultrasonic energy into the body, the needle comprising a body and a distal tip, the needle body comprising a non-circular cross-section and, a planar surface adopted to reflect the incident beam.

9. The needle of claim 8 wherein the needle body comprises a hollow body and a stylet positioned within the hollow body.

10. The needle of claim 9 wherein the planar surface is continuous along a substantial portion of the length of the needle body.

* * * * *

UNITED STATES PATENT AND TRADEMARK OFFICE
CERTIFICATE OF CORRECTION

PATENT NO. : 5,611,345
DATED : March 18, 1997
INVENTOR(S) : John F. Hibbeln

It is certified that error appears in the above-indentified patent and that said Letters Patent is hereby corrected as shown below:

On the Title Page

In column 2, line 1, under "OTHER PUBLICATIONS", change "vol." to --Vol.--.

In the Claims

In claim 8, line 5, delete "," (comma).

In claim 8, line 6, change "adopted" to --adapted--.

Signed and Sealed this

Eleventh Day of April, 2000

Attest:

Q. TODD DICKINSON

Attesting Officer

Director of Patents and Trademarks